United States Patent [19]

Soloway

[11] Patent Number: 4,565,187

[45] Date of Patent: Jan. 21, 1986

[54] LARYNGOSCOPE

[76] Inventor: David J. Soloway, 22 Alice Ave., Merrick, N.Y. 11566

[21] Appl. No.: 647,242

[22] Filed: Sep. 4, 1984

[51] Int. Cl.⁴ .............................................. A61B 1/06
[52] U.S. Cl. ..................................................... 128/11
[58] Field of Search ........................ 128/11, 10, 15, 16, 128/17, 18, 4, 6

[56] References Cited

U.S. PATENT DOCUMENTS

| 2,433,705 | 12/1947 | Palmeter | 128/10 |
| 2,646,037 | 7/1953 | Cook et al. | 128/6 |
| 2,649,087 | 8/1953 | Allyn et al. | 128/6 |
| 4,273,112 | 6/1981 | Heine et al. | 128/11 |
| 4,406,280 | 9/1983 | Upsher | 128/11 |
| 4,437,458 | 3/1984 | Upsher | 128/11 |

Primary Examiner—William H. Grieb
Attorney, Agent, or Firm—Michael I. Kroll

[57] ABSTRACT

A laryngoscope is provided and consists of a plastic disposable blade that has a hollow sleeve. The blade is removably attached to either a handle or adapter. The handle or adapter has a light emitting tube that enters the hollow sleeve so that a larynx can be illuminated and the blade will obviate dental trauma. The handle and adapter can be adjustable so that various angle arrangements can be formed by the blade with respect to the handle.

13 Claims, 14 Drawing Figures

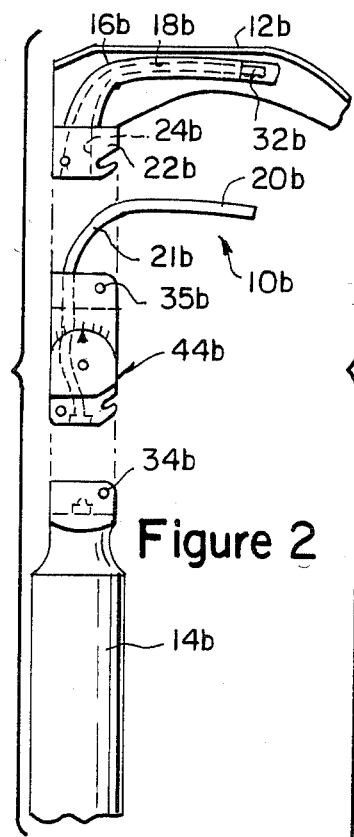
Figure 2
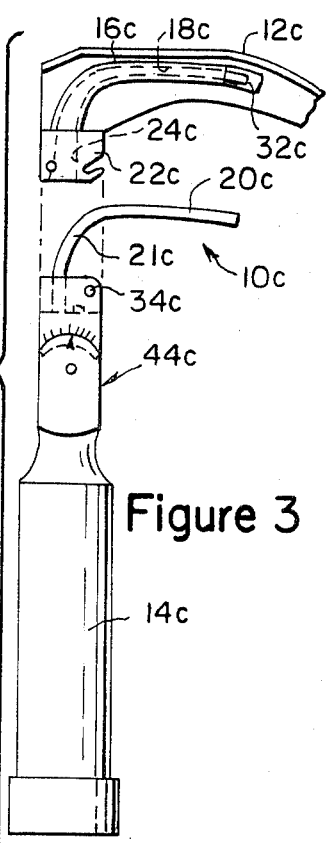
Figure 3
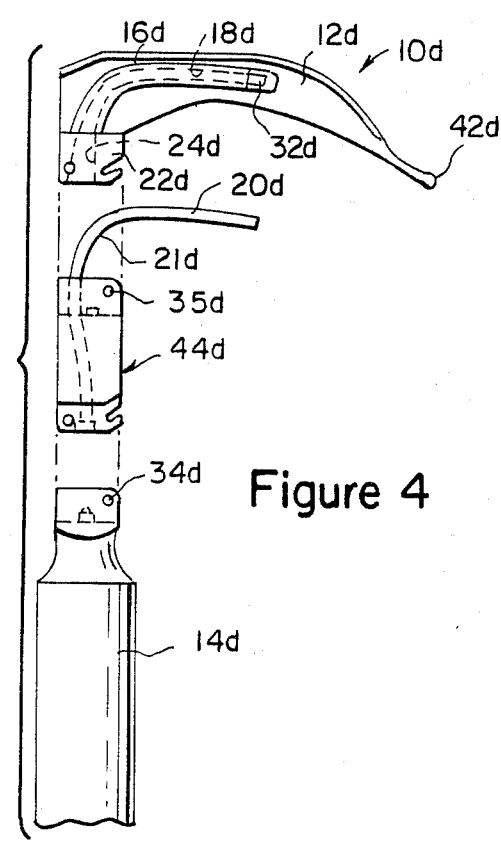
Figure 4
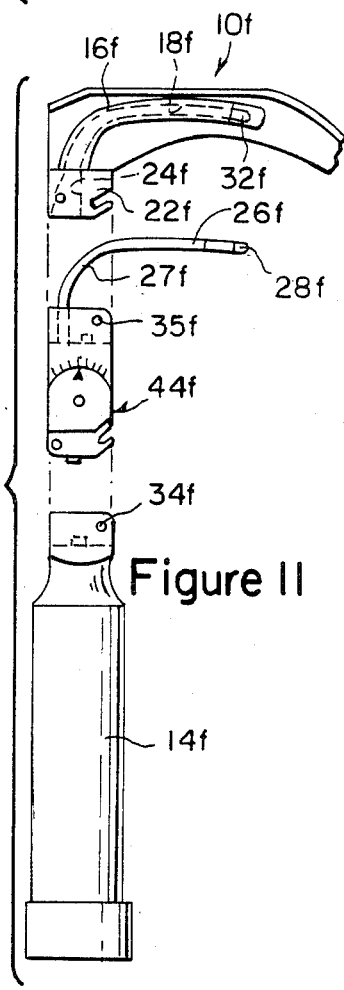
Figure 11
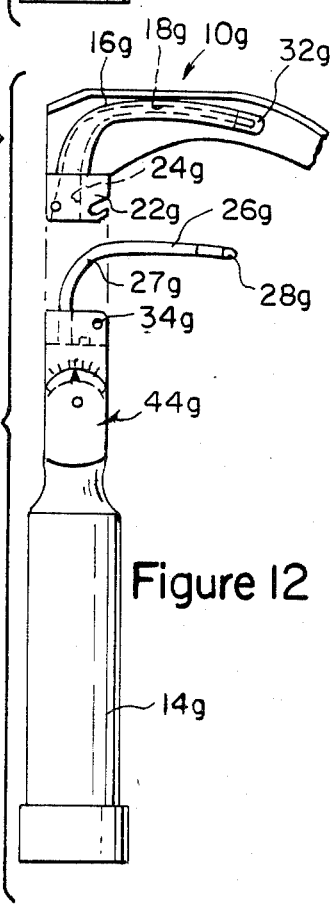
Figure 12
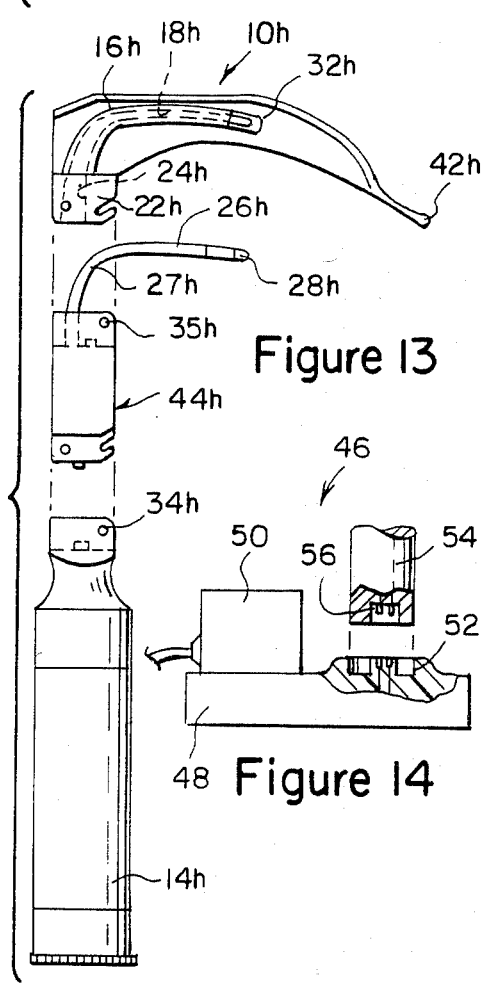
Figure 13
Figure 14

LARYNGOSCOPE

BACKGROUND OF THE INVENTION

1. Field of Invention

The instant invention relates generally to laryngoscopes and more specifically it relates to a laryngoscope that uses a plastic disposable blade.

One of the most common complications of laryngoscopy is damage to the teeth, gums or dental prosthesis. Not only may there be cosmetic disfigurement, discomfort and extensive restorative dentistry, but if the patient aspirates a dislodged tooth or fragment, there may be grave pulmonary complications.

A healthy tooth may be chipped, broken or loosened. A loose tooth may be avulsed or brittle prosthetic devices can be damaged. The incisors are most often injured and occassionally the canines are also.

This trauma usually is caused by utilization of the incisor edge of the upper anterior teeth or gums as a fulcrum point. To visualize the larynx, the patient's upper incisors are used as a pivot point for the traditional metal laryngoscope blade, providing leverage against anterior pharyngeal structures.

Traditional metal laryngoscope blades must also be designed to withstand boiling water sterilization, autoclaves or ethylene oxide with respect to prevent infectious diseases to enter the oral route.

2. Description of the Prior Art

To protect dental structures, mouth or tooth protectors have been developed. A number of devices have been created to protect both the teeth and gums, such as the Gump and Gardent tooth protectors.

It is impractical to advocate that a mouth protector should be used routinely. However, in certain instances it does seem justified as a preventive measure.

Tooth protectors do have disadvantages. They decrease the opening of the mouth and may interfere with visualization of the larynx. They may also give too great a sense of security to the laryngoscopist who may tend to use the covering as an insulation against which to pivot the traditional metal laryngoscope blade. This will result in undue pressure on the teeth with resulting damage.

As far as sterilization is concerned it is a costly and time consuming measure but must be done when using the traditional metal laryngoscope blade for maximum instrument life and performance. This situation is not desirable so accordingly it is in need of an improvement.

SUMMARY OF THE INVENTION

A principle object of the present invention is to provide a laryngoscope that uses a plastic disposable blade with respect to the prevention of transmission of infectious diseases via the oral route.

Another object is to provide a laryngoscope that uses a plastic disposable blade that obviates dental trauma.

An additional object is to provide a laryngoscope that uses a plastic disposable blade in conjunction with an adjustable or fixed angle adapter so that a regular handle can be utilized with the disposable blade.

A further object is to provide a laryngoscope that uses a plastic disposable blade in conjunction with an adjustable adapter or an adjustable handle so that various angle arrangements can be formed by the disposable blade with respect to the handle, thereby facilitating endortracheal intubation in precarious situations.

A still further object is to provide a laryngoscope that uses a plastic disposable blade that is easy to use, is economical in cost and conforms to safety performance and durability throughout its entire operation.

Further objects of the invention will appear as the description proceeds.

To the accomplishemnt of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 2 is an exploded left side view with parts broken away of a fiber-optic illumination system having a plastic disposable blade and an adjustable adapter with a flexible fiber-optic tube attached thereto.

FIG. 3 is an exploded left side view of a fiber-optic illumination system having a plastic disposable blade and an adjustable handle with a flexible fiber-optic tube attached thereto.

FIG. 4 is an exploded left side view with parts broken away of a fiber-optic illumination system having a plastic disposable blade and a fixed angle adapter with a flexible fiber-optic tube attached thereto.

FIG. 5 is a cross sectional view taken along line 5—5 through the plastic disposable blade in FIG. 1.

FIG. 6 is a bottom view of the fitting of the plastic disposable blade taken along line 6—6 in FIG. 1 with the flexible fiber-optic tube in section before the lock-in maneuver is completed.

FIG. 7 is a bottom view similar to FIG. 6 after the lock in maneuver is completed.

FIG. 8 is a partial left side view with parts broken away and in section showing installation of the flexible fiber-optic tube within the fitting of the plastic disposable blade.

FIG. 9 is a partial right side view of the front portion of the plastic disposable blade as shown in FIG. 1.

FIG. 10 is an exploded left side view with parts broken away of a conventional illumination system having a plastic disposable blade and a handle with a light bulb flexible tube attached thereto.

FIG. 11 is an exploded left side view of a conventional illumination system having a plastic disposable blade and an adjustable adapter with a light bulb flexible tube attached thereto.

FIG. 12 is an exploded left side view of a conventional illumination system having a plastic disposable blade and an adjustable handle with a light bulb flexible tube attached thereto.

FIG. 13 is an exploded left side view of a conventional illumination system having a plastic disposable blade and a fixed angle adapter with a light bulb flexible tube attached thereto.

FIG. 14 is a side view with parts broken away of a battery charger for the handle of the laryngoscope.

DETAILED DESCRIPTION OF THE PREFERRED EMBODIMENTS

Figure 1:
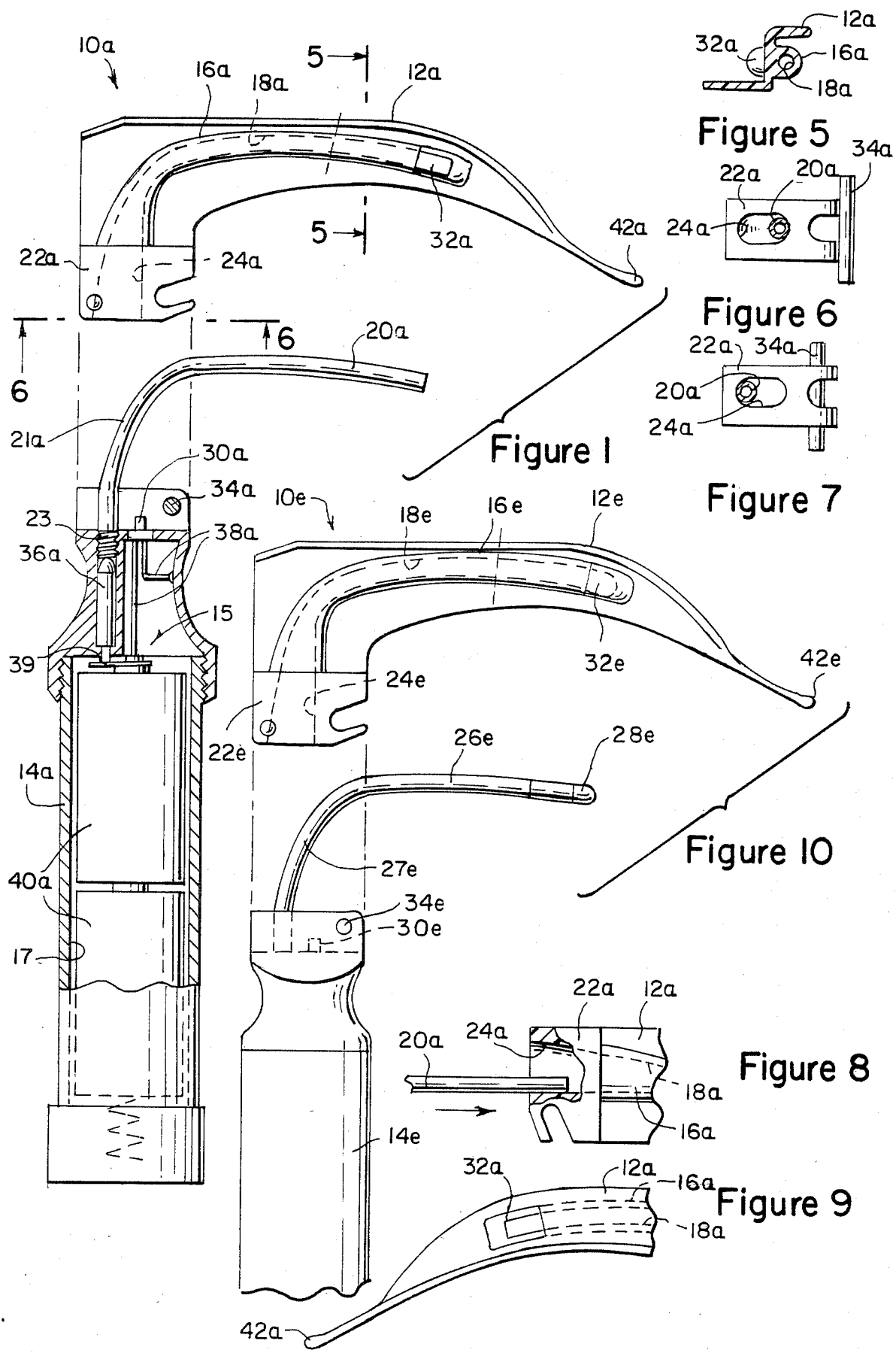
FIG. 1 is an exploded left side view partly in section of a fiber-optic illumination system having a plastic disposable blade and a handle with a flexible fiber-optic tube attached thereto.

Turning now descriptively to the drawings, in which similar reference characters denote similar elements throughout the several views, FIG. 1 illustrates a laryngoscope 10a that contains a handle 14a, an electric circuit 15, a flexible light emitting tube 20a and a plastic disposable blade 12a.

The handle 14a has a hook-on fitting 34a and a hollow chamber 17 therein. The electric circuit 15 includes a switch 30a, electrical connectors 38a, a contact plate 39, a light bulb 36a and batteries 40a. The flexible light emitting tube 20a is fiber-optic and is affixed to the handle 14a by threads 23 adjacent the hook-on fitting 34a.

The plastic disposable blade 12a has a hook-on fitting 22a and a hollow sleeve 16a. The blade 12a is removably attached to the handle 14a with the light emitting tube 20a entering the hollow sleeve 16a. A larynx (not shown) can be illuminated and the blade 12a will obviate dental trauma.

FIGS. 5 through 9 show various details of the laryngoscope 10a as shown in FIG. 1.

FIG. 3 shows a fiber-optic laryngoscope 10c wherein the handle 14c is angle adjustable at 44c so that various angle arrangements can be formed by the balde 12c with respect to the handle 14c.

FIGS. 2 and 4 show fiber-optic laryngoscope 10b and 10d that utilizes adapters 44b and 44d. The adapter 44b is angle adjustable so that various angle arrangements can be formed by the blade 12b with respect to the handle 14b. The adapter 44d is at a fixed angle so that the handle 14d and the blade 12d can be used together as a complete system.

The adapters 44b and 44d have hook-on fittings 35b and 35d and flexible light emitting tubes 20b and 20d affixed adjacent the hook-on fittings 35b and 35d. The adapters 44b and 44d are removably attached to the handles 14b and 14d. The blades 12b and 12d are removably attached to the adapters 44b and 44d with the light emitting tubes 20b and 20d entering the hollow sleeves 16b and 16d.

The laryngoscopes 10e through 10h in FIGS. 10 through 13 are identical to the laryngoscopes 10a through 10d in FIGS. 1 through 4 except that the light emitting tubes 26e through 26h contain light bulbs 28e through 28h electrically affixed to free ends thereof.

FIG. 14 shows a battery charger 46 that consists of a base 48, a transformer 50 and a female recepticle 52. A modified laryngoscope handle 54 has a male plug 56 at bottom end that mates with the recepticle 52 to recharge the alternate rechargeable batteries that are optionally contained therein.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A laryngoscope which comprises:
   (a) a handle having a hook-on fitting and a hollow chamber therein;
   (b) means for illuminating carried within said hollow chamber of said handle;
   (c) a flexible light emitting tube affixed to said handle adjacent said hook-on fitting; and
   (d) a plastic disposable blade having a hook-on fitting and a hollow sleeve, said blade is removably attached to said handle with said light emitting tube entering said hollow sleeve so that a larynx can be illuminated and said blade will obviate dental trauma.

2. A laryngoscope as recited in claim 1, wherein said flexible light emitting tube is fiber-optic.

3. A laryngoscope as recited in claim 1, wherein said flexible light emitting tube further comprises a light bulb, electrically affixed to free end thereof.

4. A laryngoscope as recited in claim 1, wherein said handle is angle adjustable so that various angle arrangements can be formed by said blade with respect to said handle.

5. A laryngoscope as recited in claim 4, wherein said flexible light emitting tube is fiber-optic.

6. A laryngoscope as recited in claim 4, wherein said flexible light emitting tube further comprises a light bulb electrically affixed to free end thereof.

7. A laryngoscope which comprises:
   (a) a handle having a hook-on fitting and a hollow chamber therein;
   (b) means for illuminating carried within said hollow chamber of said handle;
   (c) an adapter having a hook-on fitting and a flexible light emitting tube affixed adjacant said hook-on fitting, said adapter removably attached to said handle; and
   (d) a plastic disposable blade having a hook-on fitting and a hollow sleeve, said blade is removably attached to said adapter with said light emitting tube entering said hollow sleeve so that a larynx can be illuminated and said blade will obviate dental trauma.

8. A laryngoscope as recited in claim 7, wherein said flexible light emitting tube is fiber-optic.

9. A laryngoscope as recited in claim 7, wherein said flexible light emitting tube further comprises a light bulb, electrically affixed to free end thereof.

10. A laryngoscope as recited in claim 7, wherein said adapter is angle adjustable so that various angle arrangements can be formed by said blade with respect to said handle.

11. A laryngoscope as recited in claim 7, wherein said adapter is at a fixed angle so that said handle and said blade can be used together as a complete system.

12. A laryngoscope as recited in claim 1, wherein the means for illuminating comprises rechargeable batteries within said handle and a battery charger to recharge said rechargeable batteries.

13. A laryngoscope as recited in claim 7, wherein the means for illumination comprises rechargeable batteries within said handle and a battery charger to recharge said rechargeable batteries.

* * * * *